United States Patent
Lange, III et al.

(10) Patent No.: US 7,071,174 B1
(45) Date of Patent: Jul. 4, 2006

(54) METHOD AND COMPOSITION FOR INHIBITING CHOLESTEROL ESTERASE

(75) Inventors: Louis G. Lange, III, Portola Valley, CA (US); Curtis A. Spilburg, Sunnyvale, CA (US); Dayton T. Reardan, Excelsior, MN (US)

(73) Assignee: CV Therapeutics, Inc., Palo Alto, CA (US)

( * ) Notice: Subject to any disclaimer, the term of this patent is extended or adjusted under 35 U.S.C. 154(b) by 235 days.

(21) Appl. No.: 09/712,364

(22) Filed: Nov. 14, 2000

Related U.S. Application Data

(60) Continuation of application No. 08/816,823, filed on Mar. 18, 1997, now Pat. No. 6,632,801, which is a continuation of application No. 08/451,563, filed on May 26, 1995, now abandoned, which is a division of application No. 08/322,782, filed on Oct. 13, 1994, now Pat. No. 5,521,303.

(51) Int. Cl.
*A61K 31/737* (2006.01)
(52) U.S. Cl. .......................... 514/55; 514/56; 514/57
(58) Field of Classification Search ............ 514/55–57, 514/452, 529
See application file for complete search history.

(56) References Cited

U.S. PATENT DOCUMENTS

| | | | |
|---|---|---|---|
| 2,755,275 A | 1/1956 | Cushing | |
| 3,175,942 A | 3/1965 | Anderson | |
| 3,507,855 A | 4/1970 | Whistler | |
| 3,511,910 A | 5/1970 | Halleck | |
| 3,624,069 A | 11/1971 | Schweiger | |
| 3,627,872 A | 12/1971 | Parkinson | |
| 3,846,541 A * | 11/1974 | Howard ...................... | 424/79 |
| 3,956,173 A | 5/1976 | Towle | |
| 4,223,023 A | 9/1980 | Furda | |
| 4,389,523 A | 6/1983 | Okajimia et al. | |
| 4,480,091 A | 10/1984 | Brewer | |
| 4,623,539 A | 11/1986 | Tunc | |
| 4,642,313 A | 2/1987 | Matsumoto et al. | |
| 4,814,437 A | 3/1989 | deBelder et al. | |
| 4,859,703 A * | 8/1989 | Krause ...................... | 514/534 |
| 5,017,565 A | 5/1991 | Lange et al. | |
| 5,063,210 A | 11/1991 | Lange et al. | |
| 5,173,408 A | 12/1992 | Lange et al. | |
| 5,429,937 A | 7/1995 | Lange et al. | |
| 5,432,058 A | 7/1995 | Lange et al. | |
| 6,632,801 B1 * | 10/2003 | Lange et al. ................... | 514/54 |

FOREIGN PATENT DOCUMENTS

| | | |
|---|---|---|
| GB | 953626 | 3/1964 |
| GB | 1164569 | 9/1969 |
| GB | 1433732 | 4/1976 |
| GB | 1053143 | 12/1996 |
| JP | 4943937 | 11/1974 |
| JP | 138202 | 8/1984 |
| JP | 164722 | 9/1989 |
| JP | 0015435 | 2/1990 |
| WO | WO 90/12579 | 11/1990 |

OTHER PUBLICATIONS

East, C. et al "Combination Drug Therapy for Familial Combined Hyperlipidemia" Ann. Int. Med., 1988, vol. 109, pp. 25-32.*
Goto, et al., "Effect of Dextran Sulfate (MDS) on Prevention of Iscehmic Heart Disease in Double Blind Primary Prevention Trial", *J. Clin. Biochem*, 2: 55-70 (1987).
Bosner, et al., "Receptor-like Function of Heparin in the Binding and uptake of neutral lipids", *Proc. Natl. Acad. Sci.* 85: 7438-7442 (1988).
Hoffman, et al., "Studies on the Blood-Anticoagulant Activity of Sulphated Polysaccharides with Different Uronic Acid Content", *Carbohydrate Polymers*, 2: 115-121 (1982).
Cook, et al., "Comparative Pharmacology and Chemistry of Synthetic Sulfated Polysaccharides", *Arch. Int. Pharmacody.*, 1-19 (1963).

* cited by examiner

*Primary Examiner*—Leigh C. Maier
(74) *Attorney, Agent, or Firm*—CV Therapeutics, Inc.

(57) ABSTRACT

This invention encompasses methods for manufacturing purified, high molecular weight sulfated polysaccharide compositions that inhibit pancreatic cholesterol esterase and lower cholesterol in the blood stream.

6 Claims, 4 Drawing Sheets

(R = SO₃Na)

(I)

METHOD AND COMPOSITION FOR INHIBITING CHOLESTEROL ESTERASE

This is a continuation application of application Ser. No. 08/816,823 filed on Mar. 18, 1997 now U.S. Pat. No. 6,632,801, which is a continuation of application Ser. No. 08/451,563, filed May 26, 1995, now abandoned which is a divisional of application Ser. No. 08/322,782 filed on Oct. 13, 1994, now U.S. Pat. No. 5,521,303.

BACKGROUND OF THE INVENTION

This invention relates to a method for preparing a therapeutic agent that upon ingestion decreases intestinal cholesterol absorption in man and specifically inhibits or decreases intestinal cholesterol absorption by inhibiting the pancreatic cholesterol esterase catalyzed hydrolysis of naturally occurring and ingested cholesterol esters and by inhibiting the cholesterol esterase facilitated uptake of free cholesterol.

The invention is based upon the discovery that pancreatic cholesterol esterase is an important contributor to overall dietary cholesterol absorption because (1) cholesterol derived from cholesterol esters is preferentially absorbed compared to free cholesterol; (2) cholesterol esterase enhances the absorption of free cholesterol and (3) dietary cholesterol and/or cholesterol esters induce the mRNA and level of enzymatic activity of cholesterol esterase in the pancreas in a newly discovered intestinal-pancreatic cycle for the absorption of cholesterol. U.S. Pat. Nos. 5,173,408 and 5,063,210 describe the importance of cholesterol esterase in the dietary uptake of cholesterol and also disclose methods for inhibiting cholesterol esterase. Thus, the surprising usefulness of inhibiting cholesterol esterase has demonstrated a new need for potent (Ki less than 5 μM) and safe inhibitors of cholesterol esterase.

Many physical ailments are attributed at least in part to high levels of serum cholesterol. Atherosclerosis, for example, is a leading cause of death in the United States and high serum cholesterol concentrations are associated with increased risks of fatal atherosclerotic events. The discovery that the cholesterol esterase enzyme plays a role in intestinal cholesterol absorption has led to attempts to attenuate intestinal cholesterol absorption in man by inhibiting the action of the cholesterol esterase enzyme. As a result of these findings, there is now an important need to develop human pancreatic cholesterol esterase inhibitors, especially those that are not absorbed and are essentially nondegradable. The pharmacology of various polysaccharides has been investigated. Cook and Cammarata, 1963, Arch. Int. Pharmacodyn. 144: 1. In particular, crude sulfated amylopectin has been taught in U.S. Pat. No. 4,150,110 as an anti-ulcer agent, but its property as a cholesterol esterase inhibitor has not been recognized.

Sulfated dextran of low molecular weight has been recognized for use in the treatment of hyperlipemia and as an orally administered anticoagulant. British Patent No. 953, 626. In Japan, low molecular weight sulfated dextran (MDS) at a dose of 1800 mg/day has been used to reduce serum cholesterol levels by activating a blood enzyme lipoprotein lipase. Goro et al, 1987, J. Clin. Biochem. Nutr. 2: 55–70. As demonstrated by carbon-14 labelling studies, the low molecular weight of this bacterial dextran, (7–8,000 Daltons), allows the sulfated dextran to be absorbed by the intestine Drugs In Japan (Ethical Drugs, 10th ed. 1986). MDS was developed for this property of intestinal absorption as indicated by the claim that a faster reduction in serum lipids can be obtained by intravenous administration of this agent with clearance of serum lipemia due to activation of plasma lipoprotein lipase. Clearly this route of administration will not lead to effects on inhibiting cholesterol esterase in the intestine. Absorption of MDS can lead to a variety of side effects, most notably, anticoagulant effects that must be monitored. This preparation has not been known to inhibit cholesterol esterase and it is sulfated randomly and at various ring positions. High molecular weight dextran sulfate has been excluded from development by others because of its lack of absorption and its attendant inability to activate serum lipoprotein lipase.

More recently, it has been discovered that crude nonabsorbable polysaccharides sulfated at the three position of the glucopyranose ring are effective as inhibitors of cholesterol esterase. See U.S. patent application Ser. No. 08/121, 369. Useful 3-sulfated polysaccharides may be derived from the synthetic sulfation of polysaccharides from various natural sources including seaweeds.

Methods for preparing sulfated polysaccharides are also known in the art. For example, U.S. Pat. No. 3,624,069 describes the sulfation of cellulose with a sulfur trioxide/ lower n-dialkyl amide sulfation complex. U.S. Pat. No. 4,480,091 describes a process for preparing cellulose sulfate esters in a three step process. Finally, U.S. Pat. No. 4,814, 437 describes a method for preparing sulfated polysaccharides by subjecting the polysaccharide to a reducing step prior to sulfation.

SUMMARY OF THE INVENTION

The present invention is directed to a method for manufacturing high molecular weight 3-sulfated polysaccharides that are essentially non-absorbable and nondegradable in the alimentary tract, and when administered orally, they are useful in decreasing human serum cholesterol and LDL levels by inhibiting human pancreatic cholesterol esterase, now recognized as a key enzyme involved in mediating cholesterol absorption. Thus, following the methods of this invention a sulfated polysaccharide compound is prepared wherein greater than 95% of the compound has a molecular weight greater than 75,000 Daltons, the sulfate to monomer ratio is between 1.0 and 3.0, and less than 0.5% by weight of the material is free sulfate. The very high molecular weight sulfated polysaccharides manufactured by methods of this invention can be administered to humans in tablet form, incorporated in a foodstuff, or by any other method that inhibits cholesterol absorption in the alimentary tract.

DESCRIPTION OF THE PREFERRED EMBODIMENT

Figure 1:
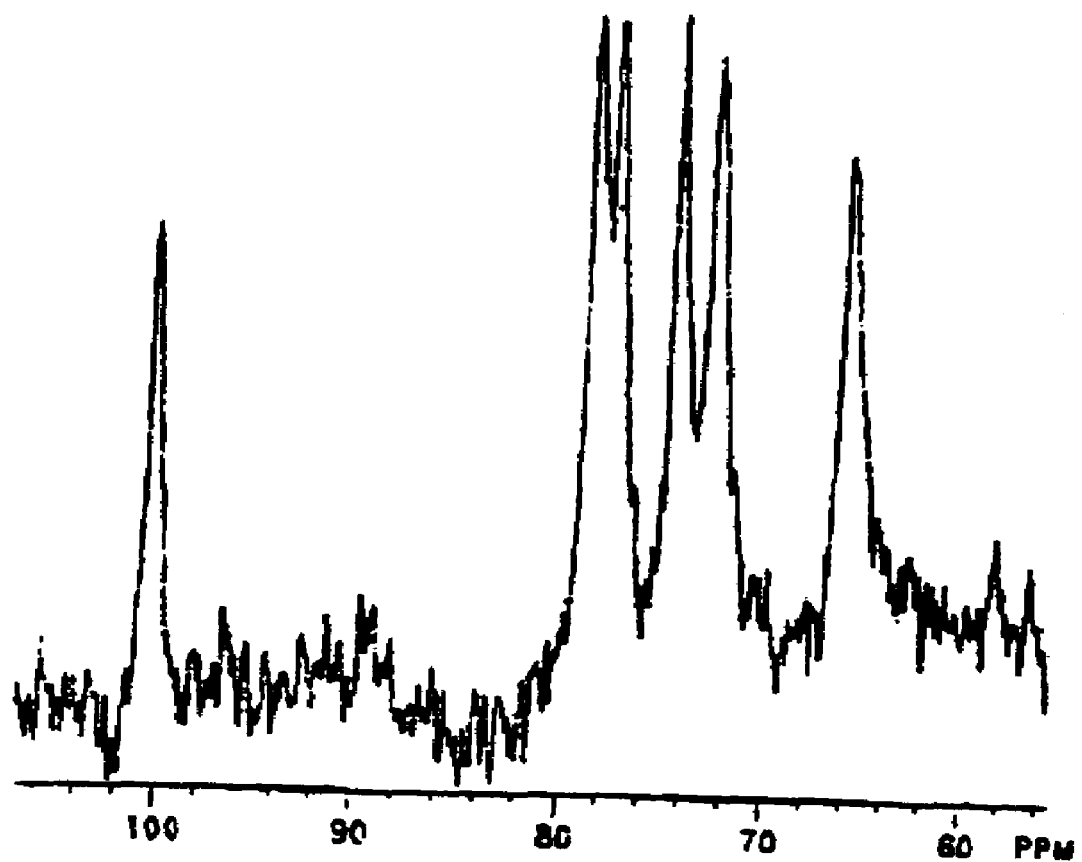
FIG. 1 is a $^{13}$C-NMR spectrum of a very high molecular weight sulfated polysaccharide of this invention.

In accordance with the present invention, we have made certain discoveries concerning approaches to inhibiting cholesterol absorption from the intestine to reduce the level of serum cholesterol and the incidence of atherosclerosis. Previously, a lack of understanding of the role that cholesterol esters play in the diet has precluded development of effective inhibitors of cholesterol esterase. Cholesterol derived from cholesterol esters represents only 10 to 15% of total dietary sterol that is absorbed, Dietschy, Intestinal Lipid Absorption in Physiology of the Gastrointestinal Tract, Vol. 2 p. 1170, Raven Press, N.Y. (1981). In addition, dietary cholesterol esters are not absorbed by the small intestine unless they are first hydrolyzed by pancreatic cholesterol esterase. Vahouny, G. & Treadwell, C. Proc. Soc. Exp. Biol. Med. 116, 496 (1964). Because of the generally accepted thesis that cholesterol esters contribute little to the total absorbed cholesterol, little attempt has been made to inhibit the intestinal absorption of cholesterol esters.

It has now been found that cholesterol derived from esters is preferentially absorbed, by more than 80%, when compared to free cholesterol. In addition, cholesterol esterase also promotes the absorption of free cholesterol. Biochemistry, 32: 12085–89 (1993). These observations demonstrate that cholesterol esterase contributes significantly to total cholesterol absorption and there is now an important need to develop inhibitors of human pancreatic cholesterol esterase.

The present invention is a non-obvious improvement over the prior art of this invention, because the very high molecular weight sulfated polysaccharides (defined below) are (1) vastly more potent inhibitors of cholesterol esterase than heparin and other low molecular weight polysaccharides which, to a small extent, inhibit the enzyme, (2) non-absorbable from the intestine, (3) inexpensive, (4) more continuously in contact with the intestinal enzyme by virtue of (1) and (2); and (5) essentially non-toxic.

Dietary intake of cholesterol is independently linked to coronary heart disease and hence intestinal cholesterol absorption is an important part of the lipid homeostatic process. The rate limiting step for intestinal cholesterol absorption is mediated by the cholesterol transport function of cholesterol esterase. This protein is unique in humans because there is a novel exon 11 in the gene, a unique C-terminal extension of the protein and a unique inhibitory site in the primary structure. Kumar et al., 1 Biochemistry 31, 6077 (1992). Large 3-sulfated polysaccharides bind to this unique sequence producing potent inhibition with $IC_{50}$'s in the sub-nanomolar range for the human enzyme. One of these inhibitors, very high molecular weight cellulose sulfate prepared by the method of this invention, has an $IC_{50}$ of 20 pM towards the human target and 100,000 pM towards rabbit cholesterol esterase. High molecular weight sulfated cellulose (1.5 million Da) is not absorbed from the intestine, and it inhibits cholesterol uptake into cultured human Caco-2 cells. Cellulose sulfate decreases serum cholesterol levels in the normal chow-fed rabbit, indicating inhibition of reabsorption of hepatically secreted cholesterol. In cholesterol fed rabbits, administration (100 mg/kg) of very high molecular weight cellulose sulfate (1) decreases cholesterol absorption by 80%, (2) decreases serum cholesterol by over 50% and (3) decreases hepatic cholesterol by over 30%. These data indicate that small doses of cellulose sulfate having a molecular weight greater than about 500,000 Daltons is an effective pharmaceutical agent to decrease serum cholesterol levels and LDL levels.

Free sulfate and low molecular weight sulfated polysaccharides are undesirable byproducts of the manufacture of very high molecular weight sulfated polysaccharides. In fact, the presence of toxic, low molecular weight sulfated polysaccharides or inorganic sulfate in high molecular weight sulfated polysaccharide compositions obviated their use as an ingestible or injectable drug for any purpose. Therefore, the very high molecular weight sulfated polysaccharide of this invention must include less than 0.5 wt % free sulfate and moreover, it must contain less than 5% by weight of sulfated material having a molecular weight less than 75,000 Daltons.

We have found a method to recover pure, very high molecular weight sulfated polysaccharides that eliminates the toxic, low molecular weight polysaccharide and free sulfate by products. This method produces a new very high molecular weight sulfated polysaccharide composition of matter which is an extremely useful inhibitor of the cholesterol esterase mediated absorption of cholesterol.

The very high molecular weight sulfated polysaccharides of this invention are characterized as follows:

| Property | |
|---|---|
| Appearance | Off-White Powder |
| Sodium content | 11.0–15.0 wt % |
| Carbon content | 14.0–17.0 wt % |
| Hydrogen content | 2–3.5 wt % |
| Nitrogen content | <0.5 wt % |
| Sulfur content | 16.0–19.0 wt % |
| Degree of sulfation | 2 ± 1.0 |
| % Free Sulfate | <0.50% |
| Specific Activity | $<2 \times 10^{-4}$ mg/ml |
| Viscosity | >4000 centipoise |
| pH on dissolution | 6–9 |
| Wt. % with Molecular Wt. >75,000 | >95% |
| Average Molecular Wt. | >500,000 Daltons |

Very high molecular weight sulfated polysaccharides of this invention are made by the following steps: (1) prepare an anhydrous DMF suspension of a high molecular weight polysaccharide or cellulose from a source such as cotton linters; (2) mix the anhydrous DMF suspension of high molecular weight polysaccharides or cellulose with a sulfur source such as a sulfur trioxide/DMF complex; (3) neutralize the acidic mixture after the sulfation reaction is essentially complete to give a crude sulfated polysaccharide mixture including crude sulfated polysaccharides and aqueous reactants; (4) separate crude, very high molecular weight sulfated polysaccharides from the aqueous crude sulfated polysaccharide mixture; (5) wash the separated crude very high molecular weight sulfated polysaccharides; and (6) dry the resulting crude intermediate product.

The dried crude intermediate product is then purified to exclude essentially all impurities such as free sulfates and sulfated polysaccharides having a molecular weight less than 75,000 Daltons. Purification is preferably accomplished by dissolving the dried crude intermediate product in water to form an aqueous crude solution containing very high molecular weight sulfated polysaccharides and impurities including free sulfate and low molecular weight sulfated products having molecular weights less than 75,000 Daltons. The crude aqueous solution is subjected to a first filtration step to produce a very high molecular weight sulfated polysaccharide containing filtrate essentially free of unreacted polysaccharides and/or fines. Preferably the first filtration step consists of at least two successive filtration steps; the first across a 5 micron filter and the next across a smaller filter and so forth until the final filtration step which preferably uses a 1 micron filter.

The filtrate produced in the first filtration step is then diafiltered in a second filtration step with a 500,000 Dalton molecular weight cut-off membrane against deionized water to produce a purified very high molecular weight sulfated polysaccharide product. The diafiltration step eliminates free sulfates, bicarbonate, and essentially eliminates low molecular weight sulfated polysaccharides having molecular weights less than 75,000 Daltons that remain in the filtrate from the first filtration step. The aqueous purified product is preferably dried before it is used. Any drying process known in the art, such as spray drying, drum drying, fluid bed granulation, or lyophilization, that is capable of producing powder from an aqueous solution containing dissolved solids may be used.

In accordance with the present invention, we have made certain discoveries concerning structural features of very high molecular weight sulfated polysaccharide human pancreatic cholesterol esterase inhibitors (molecular weight greater than 75,000 Daltons) prepared from non-mammalian and non-bacterial polysaccharides. These include discoveries as to the synthesis and characteristics of sulfated polysaccharides that render highly specific derivatives with subnanomolar inhibitory constants toward human cholesterol esterase, which, along with their large size, makes them essentially nonabsorbable and non-degradable. For example, the very high molecular weight sulfated polysaccharides of this invention do not activate the plasma enzyme lipoprotein lipase after oral use. Thus, these sulfated polysaccharides act to reduce the cholesterol esterase facilitated absorption of cholesterol by multiple mechanisms, for example by (1) inhibiting enzymatic cleavage of cholesterol esters, (2) displacing enzyme from its binding site on the intestinal cell, and (3) inhibiting transport of free cholesterol into the small intestinal cell. In addition, these agents, unlike tetrahydrolipostatin, do not cause steatorrhea in effective doses given to animals.

While a number of structural features can modulate the degree of inhibition, the presence of a 3-sulfate markedly enhances inhibition. Furthermore, not all sulfated polysaccharides inhibit cholesterol esterase. Chondroitin sulfate, for example, is not inhibitory in its native state. The repeating unit in this polysaccharide consists of two substituted glucopyranose-like rings linked through the hydroxyl group at the 3-position of one to the hydroxyl group at the 1-position of the other. Therefore, the dimeric repeat unit has only one unsubstituted hydroxyl group at the 3-position. When this polysaccharide is sulfated, it becomes a potent inhibitor of human cholesterol esterase, indicating that the presence of a 3-sulfate on the glucopyranose ring is both necessary and sufficient for producing inhibitory activity. On the other hand, the presence of a 2-sulfate decreases inhibition while a 6-sulfate is unnecessary.

The efficacy of sulfated polysaccharides for decreasing cholesterol absorption is increased by reducing the absorption of the sulfated polysaccharide from the intestine and thus prolonging its contact with the enzyme, among other things. Very high molecular weight sulfated polysaccharides are poorly absorbed and, therefore, are necessary and sufficient to inhibit the absorption of cholesterol. The increased molecular weight also increases the inhibitory activity of the polysaccharides and sulfation increases the solubility and access to enzyme to produce greater inhibition. For example, low molecular weight dextran sulfate (MW=5000 Daltons) exhibited an $IC_{50}$ of 20 nM while the $IC_{50}$ of high molecular weight sulfated polysaccharides (MW=500,000 Daltons) was 0.02 nM. Accordingly, the present invention includes very high molecular weight sulfated polysaccharide compounds of the formula:

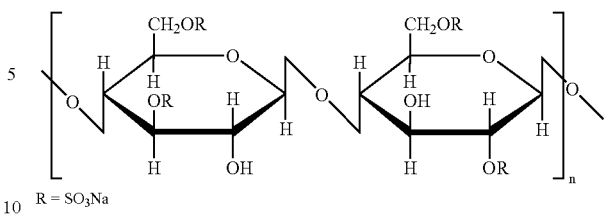

R = SO$_3$Na

The chemical formula for a monomeric unit is $C_6H_8Na_2O_{11}S_2$, wherein n is 1400 or greater and wherein R is —SO$_3$Na.

Cellulose sulfate is preferably used in preparing a very high molecular weight sulfated polysaccharide of this invention which is manufactured in three basic steps: (1) sulfation of chemically pure cellulose using sulfur trioxide in dimethyl formamide; (2) filtration to remove water insoluble contaminants and diafiltration against 500,000 Dalton molecular weight or greater cut-off membranes to remove potentially toxic small molecular weight contaminants; and (3) an optional formulation step to produce a tablet, capsule, liquid or foodstuff comprising a very high molecular weight sulfated polysaccharide for human consumption.

The very high molecular weight sulfated polysaccharide of this invention may be taken in doses ranging from about 10 mg to about 5,000 mg and higher immediately before, with, or after meals, three times per day. The very high molecular weight sulfated polysaccharide functions by inhibiting the cholesterol esterase mediated absorption of cholesterol resulting in a lowering of its concentration in human blood serum.

A preferred very high molecular weight sulfated polysaccharide of this invention is cellulose sulfate consisting of chemically pure cotton cellulose linters which have been sulfated in a preferred ratio of about two moles of sulfate per mole of monomer. Cotton linter is a preferred source of cellulose since it is the most chemically pure form of commercial cellulose yet discovered. Cotton linter consists of glucose units polymerized to a total of about 14.000 monomer units with a molecular weight of about 2.4 million.

In essence, our discovery leads to a practical method for converting naturally occurring very high molecular weight polysaccharides and preferably cellulose polymers, often regarded as waste, into a highly potent, cheap, non-absorbed (they do not activate plasma lipoprotein lipase after oral administration), non-toxic, and nondegradable inhibitors of cholesterol that can be administered as soluble agents in small and well-tolerated quantities. Those skilled in the art will recognize that methods to disperse and/or enhance or prolong the presence in the intestine of inhibitors to increase their contact with cholesterol esterase will further decrease the absorption of cholesterol.

The very high molecular weight sulfated polysaccharide inhibitor manufactured by the methods of this invention can also be administered in combination with inhibitors of ACAT, acyl CoA: cholesterol acyltransferase. These compounds can lower cholesterol especially in animals (Largis et al. 1989), but they possess a number of toxic side effects since they are absorbed and are not inert. Side effects can be lowered by reducing their dosage while maintaining efficacy in combination with inhibitors of cholesterol esterase that are not absorbed. A person skilled in the art will also recognize that various ACAT inhibitors, such as, for example, that described in Heider et al., J. Lipid Res. 24: 1127 (1983), can be combined with the very high molecular weight sulfated polysaccharides of the present invention to reduce serum levels of cholesterol.

In addition, the very high molecular weight sulfated polysaccharide inhibitors of cholesterol esterase can be administered in combination with cholesterol synthesis blockers. Humans treated with cholesterol synthesis blockers experience various toxic side effects, which can be reduced by decreasing the dose administered to the patient. Therefore, administering the sulfated polysaccharide of the present invention in combination with drugs that are absorbed by the intestine and block the endogenous synthesis of cholesterol allows for decreased dosages of cholesterol synthesis blockers to obtain the same end result. The toxicity associated with cholesterol synthesis blockers can be effectively reduced while still reducing serum cholesterol levels.

Persons having skill in the art will recognize various cholesterol synthesis blockers, such as, for example, lovastatin, which can be combined with the sulfated polysaccharides of the present invention to reduce serum levels of cholesterol.

The very high molecular weight sulfated polysaccharide inhibitors of cholesterol esterase manufactured by the methods of this invention can be administered in various pharmaceutical dosage forms such as tablets, capsules, liquids and powders, alone or in the presence of one or more pharmaceutical excipient such as surfactants, flavoring agents, coloring agents, starch, sugars and the like excipients. The very high molecular weight sulfated polysaccharides of this invention can also be incorporated into food products such as biscuits and cookies. In essence, the very high molecular weight sulfated polysaccharides of this invention can be used as a dietary supplement to reduce cholesterol absorption, especially from foods rich in cholesterol and/or cholesterol esters where an unexpectedly large benefit would be obtained. Those skilled in the food and pharmaceutical arts will recognize a wide variety of formulations and vehicles for administering sulfated polysaccharides.

Preferably, very high molecular weight sulfated polysaccharides are administered to humans at or about (within about a half hour of) the time of food intake and especially with foods that are rich in cholesterol esters and/or free cholesterol. In addition, these high molecular weight sulfated polysaccharides inhibit cholesterol introduced into the intestine from bile.

The invention is illustrated further by the following examples which are not to be construed as limiting the invention in scope or spirit to the specific procedures described in them.

EXAMPLE 1

This example details a method for manufacturing a very high molecular weight sulfated polysaccharide of this invention that is useful in inhibiting cholesterol absorption.

A purified very high molecular weight sulfated polysaccharide is prepared by sulfating cellulose using sulfur trioxide dimethylformamide (DMF/SO$_3$) complex in anhydrous dimethylformamide (DMF) solvent according to the following method.

A. Dried cotton linters (8.75 kg) were shredded using a commercial paper shredder and soaked in 208 liters of dry DMF under a blanket of nitrogen. The mixture was cooled to 8–10° C.

B. After 3 hours, 33 kg of DMF/SO$_3$ complex were added with stirring. The reaction temperature was maintained between 15° C. and 20° C. for 150 min.

C. Solid sodium bicarbonate (51 kg) was added to the combined mixture and allowed to mix for 10 minutes to neutralize any excess acid. This was followed by 15 L of deionized water. Finally, acetone was added (95 L) and the mixture stirred overnight.

D. The next day, the reaction mixture was spun in a centrifuge, and the solid collected and resuspended in 208 L of acetone. The resuspended mixture was spun again in the centrifuge.

E. The solid recovered from the centrifugations was dried on a drying table overnight.

F. The crude dried sulfated polysaccharide was dissolved in water (600–1000 L) so the solution was about 0.5–1.0 wt % solids.

G. The mixture was sequentially filtered using a 50 micron, 5 micron, and 1 micron filter. A diafiltration apparatus equipped with 500,000 Dalton molecular weight cutoff membranes (Koch Membranes, pm 500 A) was then used to diafilter the 1 micron filtrate against deionized water to an effluent conductivity of <300 mS/cm.

H. The diafiltered solution was dried (in a spray drier or drum drier) and the resulting very high molecular weight sulfated polysaccharide of this invention was collected in containers of appropriate size for storage and shipment.

The very high molecular weight sulfated polysaccharides exhibited the following properties (the average values for nine manufacturing runs):

TABLE I

| Property | Result |
| --- | --- |
| Appearance | Off White |
| Specific Rotation of Hydrolysate | 16.4° |
| Degree of Sulfation | 2.06 |
| % Free Sulfate | 0.18% |
| Dimethylformamide | 18 ppm |
| Potency (IC$_{50}$) | 24 ng/ml |
| Molecular Wt. | 3,800,000 Daltons |
| % Low Molecular Weight Sulfated Cellulose | 0.67% |

EXAMPLE 2

Nuclear magnetic resonance (NMR) spectroscopy is the standard method for structural analysis of organic molecules. While this technique is widely used for structure elucidation of small molecules, there are a number of problems which make this method of limited usefulness for large molecules, such as the very high molecular weight sulfated polysaccharides of this invention.

$^{13}$C NMR Spectra.

Figure 2:
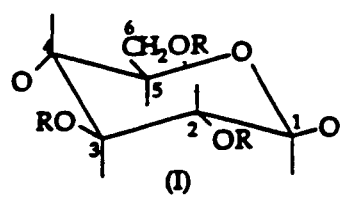
FIG. 2 shows possible structures of sulfated cellulose of this invention.
Figure 2:
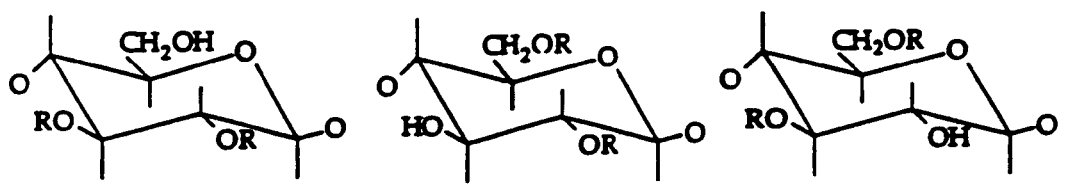
Figure 2:
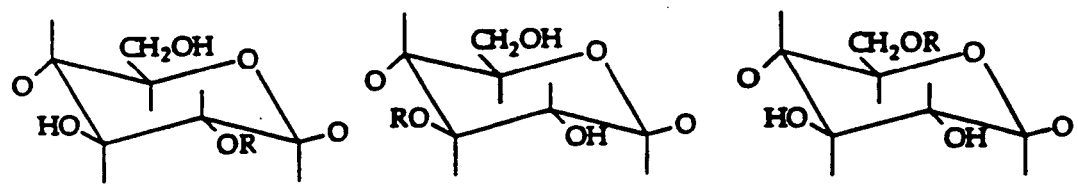
Figure 2:
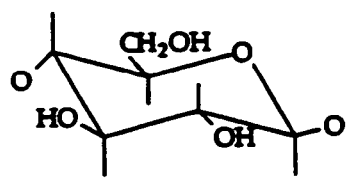

The $^{13}$C spectrum (90 MHz) of a very high molecular weight sulfated polysaccharide produced by the method of Example 1 is shown in FIG. 1. The eight different structural possibilities for any given saccharide of the very high molecular weight sulfated polysaccharides should give rise to 48 signals. (FIG. 2). However, since the observed spectrum produces only six well-defined signals, there is much overlap, making definitive assignments for all the carbon atoms impossible. The position and intensity of these various resonances are summarized below for the compound of Example 1.

TABLE II

$^{13}$C NMR CHEMICAL SHIFTS

| CHEMICAL SHIFT, ppm | INTEGRATED INTENSITY |
|---|---|
| 100.2 | 10.00 |
| 78.5, 77.4 | 29.39 |
| 74.4, 72.5 | 33.00 |
| 66.0 | 14.85 |

Even though some assignments are controversial, See Kamide, K. and Okajima, K. (1981) *Polymer Journal* p. 163–166 and Kowasaka, K. Okajima, K. and Kamide, K. (1991) *Polymer Journal*, p. 823–836, from studies on model compounds, there is agreement on the spectroscopic behavior of carbon 1 and carbon 6. For example, in going from β-D-glucopyranose to the corresponding 6-sulfate derivative, signals at these two positions shift in a characteristic way. From data on this model compound, it can be predicted with confidence that the chemical shift at 100.2 ppm observed in the analyzed compound is most likely due to carbon 1. Moreover, in the starting unsubstituted saccharide there is a resonance that is shifted by 6.6 ppm in the sulfated derivative. Taken together, this indicates that the resonance in native cellulose which occurs at 60.5 ppm and is shifted to 66.0 ppm on sulfation is due to carbon 6. Based on this, it may be concluded that the very high molecular weight compound analyzed is totally sulfated at position 6 since there is no evidence of a signal at around 60.5 ppm. This is also verified by the integrated intensity (14.85) of this signal, which corresponds to only one carbon atom. If the integrated intensities at 72.5 ppm, 74.4 ppm, 77.4 ppm, and 78.5 ppm are summed, the total (62.4) is about four times that from carbon 6. This indicates that these signals are derived from carbons 2, 3, 4 and 5 in the various mono-, di-, tri- and unsubstituted forms. Finally, the signal at 100.2 ppm from carbon 1, which is only ⅔ the intensity of the others has a lower value because of a longer relaxation time.

Since carbon 6 is sulfated in all the anhydro glucopyranose units, the number of contributing structures to the $^{13}$C NMR spectrum is diminished. It is also believed that the resonances from carbon 1 and sulfated carbon 6 are the same in all contributing structures, (See Kowansaka, K. Okajima, K. and Kamide, K. (1991) *Polymer Journal*, p. 823–836), reducing the number of magnetically non-equivalent carbons from 48 to 16. Since there are only 4 resonances to account for in the remaining 16 structures, it is still not possible to determine the relative proportions of sulfation at carbons 2 and 3.

To summarize, it is clear that carbon 6 is, within the limits of this analysis, totally sulfated. Since the polysaccharide contains more than one sulfate per monomer, the other sulfate is distributed between carbons 2 and 3.

EXAMPLE 3

This example details a method for isolating the human cholesterol esterase enzyme for use in testing the potency of very high molecular weight sulfated polysaccharides of this invention.

S-Sepharose Column Preparation

An S-Sepharose suspension (150 ml) was poured into a 250 ml graduated cylinder and the gel was allowed to settle. The supernatant was then poured off and 100 ml of a 25 mM acetic acid solution, pH 5.1, was added to the cylinder. The cylinder was covered with parafilm and the gel resuspended by gently inverting the graduate several times. The resuspended S-Sepharose was poured into a column in one application and allowed to settle under gravity. When the resin settled, the bottom of the column was opened and the buffer was drained through the resin until 1–2 cm of buffer remained over the resin bed.

S-Sepharose Chromatography

Breast milk (200 ml) stored at −20° C. and thawed to room temperature was transferred to a 250 ml beaker equipped with a stir bar. The pH was adjusted to 5.1 by the dropwise addition of 1M acetic acid. The milk was centrifuged at 15,000 rpm for 30 minutes at 4° C., and the clear solution was carefully removed from the upper fat layer. Residual fat and insoluble material were removed by passing the solution through a 0.8 micron filter.

The S-Sepharose column was filled with filtered breast milk, and the sample was applied under gravity feed. When all the sample had been added to the resin, the sides of the column were washed twice with 25 ml of 25 mM acetic acid, pH 5.1, followed by 400 ml of a 300 mM NaCl/25 mM acetic acid solution, pH 5.1. The absorbance at 280 nm of the effluent was then checked using a spectrophotometer. If the absorbance was greater than 0.025, the resin was washed with additional 50 ml aliquots of the 300 mM NaCl/25 mM acetic acid buffer solution until the absorbance was less than 0.025.

Cholesterol esterase was removed from the resin at a flow rate of 60 ml/hr using a 300 ml salt gradient increasing from 300 mM NaCl/25 mM acetic acid, pH 5.1, to 1.0 M NaCl/25 mM acetic acid, pH 5.1. Fractions were collected every 2 to 4 minutes and the absorbance at 280 nm of every other fraction was determined as well as the enzymatic activity using p-nitrophenyl butyrate as substrate. Momsen, W. & Brockman, H. (1977) Biochim. Biophys. Acta 486, 103–113. All fractions with a hydrolytic activity greater than 0.030 Abs/min were pooled in a graduated cylinder and the volume was doubled with 10 mM NaCl/20 mM acetic acid, pH 5.1. The sample was transferred to a dialysis tube (MW cutoff—12–14,000 Daltons) and dialyzed at 4° C. against three changes of 4 L of 10 mM NaCl/25 mM acetic acid, pH 5.1.

SP-Sephadex Chromatography

SP-Sephadex C-25 (10 g) was swollen in 10 mM NaCl/25 mM acetic acid, pH 5.1, and poured at 4° C. into a 2.6×40 cm glass column. The dialyzed, partially purified cholesterol esterase was pumped onto the SP-Sephadex column at 60 ml/hr, and the resin was washed with 100 ml of 10 mM NaCl/25 mM acetic acid pH 5.1. The enzyme was removed with 200 mM NaCl/25 mM acetic acid, pH 5.1. Forty fractions were collected, and the absorbance at 280 nm of every other fraction was determined as well as the enzymatic activity using p-nitrophenyl butyrate as substrate.

Assessment of Homogeneity and Storage

Polyacrylamide gel electrophoresis (8%) was used to assess the purity of samples from the SP-Sephadex column by the method of Laemmli, U.K. *Nature*, 227: 680 (1970). To avoid overloading the gel, 0.02 optical density units was removed from each fraction, using the following formula:

Volume removed (ml)=0.02/Abs

Protein was visualized with the 0.2% Coomassie Brilliant Blue.

Dilution and Storage of Enzyme Aliquots

Those fractions which gave a single band at 110 kDa were pooled and frozen at −80° C. The absorbance at 280 nm of this pool was adjusted with 200 mM NaCl/25 mM acetic acid solution, pH 5.1, to give a final value of 0.070. The protein solution was then divided into 100 µl aliquots and stored frozen at −80° C. until ready for use.

EXAMPLE 4

This example describes a method for measuring the potency, ($IC_{50}$), of very high molecular weight sulfated polysaccharides.

The non-absorbable, very high molecular weight sulfated polysaccharides of this invention are potent inhibitors of the human cholesterol esterase (CEase)—catalyzed hydrolysis of cholesterol oleate. To determine the $IC_{50}$ of inhibition, increasing amounts of sulfated polysaccharides are included in an enzyme assay, and the concentration which produces 50% inhibition is defined as the $IC_{50}$.

A 1 mg/ml solution of high molecular weight sulfated polysaccharide in 10 mM Tris (pH 7.5) buffer was diluted serially with 10 mM Tris (pH 7.5) to give solutions ranging in concentration from $1\times10^{-1}$ mg/ml to $1\times10^{-6}$ mg/ml. Thirty microliters of each diluted solution were added to a series of test tubes; 30 µl of 10 mM Tris (pH 7.5) were added to a test tube labelled "Enz Control"; and 50 µl of 10 mM Tris (pH 7.5) were added to a test tube labelled "Blk." Substrate solution (250 µl) containing cholesterol [$^{14}$C]-oleate vesicles and sodium taurocholate in 150 mM Tris, pH 7.5, were prepared as described and pipetted into each of the test tubes described above. Cox, D., Leung, C. K. T., Kyger, E., Spilburg, C., & Lange, L. (1990) Biochemistry 29, 3842. Human CEase, prepared as described in Example 3, was removed from the −80° C. freezer, thawed in an ice water bath and diluted with 400 µl of buffer consisting of 1 part 150 mM Tris, pH 7.5, and 7 parts 100 mM sodium taurocholate in 150 mM Tris, pH 7.5. A 20 µl aliquot of CEase was then added to the test tubes, except the one labelled "Blk," and the test tube rack was placed immediately in a 37° C. water bath. After ten minutes, the test tube rack was plunged into an ice water bath and the assay was completed as described elsewhere Cox, D., Leung. C. K. T., Kyger, E. Spilburg, C. & Lange. L. (1990) Biochemistry 29, 3842.

To calculate the percent activity, the following formula was used:

$$y = \text{Percent Activity} = \frac{CPM \text{ Sample} - CPM \text{ "BLK"}}{CPM \text{ "ENZ Control"} - CPM \text{ "BLK"}}$$

Using y as % activity and c as the concentration of very high molecular weight sulfated polysaccharide in the assay, the data were plotted according to the following function:

$$\log c = \log (1/y - 1)$$

The best straight line was drawn through the data points, and the $IC_{50}$ was defined as the antilog of the x-intercept.

EXAMPLE 5

This example describes methods for characterizing the very high molecular weight sulfated polysaccharides of this invention.

Determination of Degree of Substitution

Dowex-50W ion-exchange resin ($H^+$ form, dry mesh 200–400; 8% cross linkage) was added with gentle swirling to a 100 ml beaker containing 50 ml of deionized water. The water was removed and the procedure was repeated two more times. The resin was added to a 1.0×20 cm column to a bed height of 18 cm, and the column was washed with 25 ml of deionized water using a peristaltic pump at a flow rate of 30 ml/hr.

A 1.0 mg/ml solution (15 ml) of a very high molecular weight sulfated polysaccharide in water was pumped onto the resin and 5 minute fractions were collected. When all of the sample was applied to the resin, the pH of each fraction was measured with a calibrated pH electrode. Those fractions with a pH less than or equal to 3.5 contained protonated sulfated polysaccharides and were pooled in a 50 ml glass beaker.

A rinsed conductivity electrode was immersed in the beaker containing the protonated sulfated polysaccharide and the initial conductivity reading was recorded. The solution was titrated by recording the conductivity after each addition of 100 µl of 0.1 N NaOH. As base was added, the conductivity decreased until the equivalence point was reached, then the conductivity increased. The equivalence point was determined by drawing a straight line through the descending data points and a straight line through the ascending data points. The intersection point of the two lines is the equivalence point, expressed as mls of 0.10 N NaOH.

After completion of the titration, the amount of sulfated polysaccharide present was determined spectrophotometrically using Toluidine Blue. In detail, 200 µl of sulfated polysaccharide solutions, ranging in concentration from 2.5 µg/ml to 40 µg/ml, were pipetted into test tubes. A blank was prepared which contained only 200 µl of water, and various aliquots were removed from the titration and the volume was adjusted to 200 µl by adding an appropriate volume of water. After adding 10 µl of 1 mg/ml Toluidine Blue to each tube, the absorbance was read at 540 nm, after zeroing against the blank. A standard curve was prepared and the amount of sulfated polysaccharide in a sample was determined from the linear portion of the curve. Using this value and the equivalence point, the % sulfate can be determined from the following relation:

$$\% \; SO_3 = \frac{(8 \times \text{mls NaOH equivalence pt.})}{(\text{mg sulf. polysaccharide toluidine blue assay})}$$

The degree of substitution is defined as the number of hydroxyl groups on the polysaccharide that have been replaced by the $OSO_3H$ functional group. Every OH group which is lost is replaced by an $OSO_3H$ group, increasing the molecular weight by 80. Since the molecular weight of a starting cellulose monomer is 161, the molecular weight (MW) increases according to the following relation, where x=degree of the substitution:

$$MW = 161 + 80x$$

As sulfate is introduced into the polymer its percentage (y) changes according to the following relation:

$$y = 80x/(161+80x)$$

When this equation is solved for x, the degree of substitution can be calculated from the percent $SO_3$ in the sample.

$$x = 161y/80(1-y)$$

Molecular Weight Determination

The molecular weight profile of a very high molecular weight sulfated polysaccharide is determined by aqueous gel permeation chromatography using a glucose-polydivinyl benzene GPC-HPLC column. Since the sulfated polysaccharide of this invention has a very high molecular weight and viscosity, the column is run at elevated temperatures to lower the viscosity to prevent pressure problems. Importantly, columns of this type can be calibrated using standards of known molecular weight, allowing the molecular weight of an unknown sample to be determined by comparing its elution volume to those of samples of known molecular weight. This HPLC assay is used to determine the molecular weight range of a high molecular weight sulfated polysaccharide and a cumulative weight fraction plot is used to calculate the percentage low molecular weight compounds.

A mobile phase solution was prepared by adding 200 ml of DMSO to 800 ml of 0.1 M NaOH and then the solution was filtered through a 0.2 µm filter. Molecular weight standard solutions were prepared by dissolving individual molecular weight standards in mobile phase solution to yield a concentration of 1 mg/ml. Finally, a sample solution of a very high molecular weight sulfated polysaccharide was prepared by dissolving the sulfated polysaccharide in the mobile phase solution to yield a concentration of 1 mg/ml. The samples were analyzed by injecting 500 µl of each individual standard in descending order of molecular weight value and then injecting 500 µl of the sample solution. The column was operated at 80° C.

A standard curve was prepared by plotting $\log_{10}(M_p)$ of the standards with known molecular weight versus their elution time. The equation describing the standard curve was calculated by the method of least squares. The $\log_{10}(M_p)$ of the sulfated polysaccharide sample was then determined from its elution time and the derived equation.

The percentage of low molecular weight sulfated compounds is calculated using the following equation:

% Low Molecular Weight=$(AUC_{small}/AUC_{total})*100$

Where:
- $AUC_{total}$=integration of the total area under the curve of the sample peak.
- $AUC_{small}$=integration of the area under the curve of the sample peak from the elution time of the 75,000 Daltons standard to the end of the curve.

EXAMPLE 6

Infra-red spectroscopy is used to verify the presence of sulfated groups in the very high molecular weight sulfated polysaccharides prepared by this invention. This example details the method to produce a Fourier transform infrared (FTIR) spectrum of very high molecular weight sulfated polysaccharides prepared by the methods of this invention.

A sulfated polysaccharide/potassium bromide sample pellet was prepared by adding approximately 5 mg of solid sulfated polysaccharide and 495 mg of oven dried KBr into a polystyrene vial containing one plexiglass ball. The solids were mixed with a Wig-L-Bug (International Crystal Laboratories), and 200 mg were loaded into a pellet die. A clear pellet was prepared by subjecting the evacuated die to 6 metric tons of pressure for 10 minutes. The clear pellet was removed from the die and placed in the FITR sample chamber.

Figure 3:
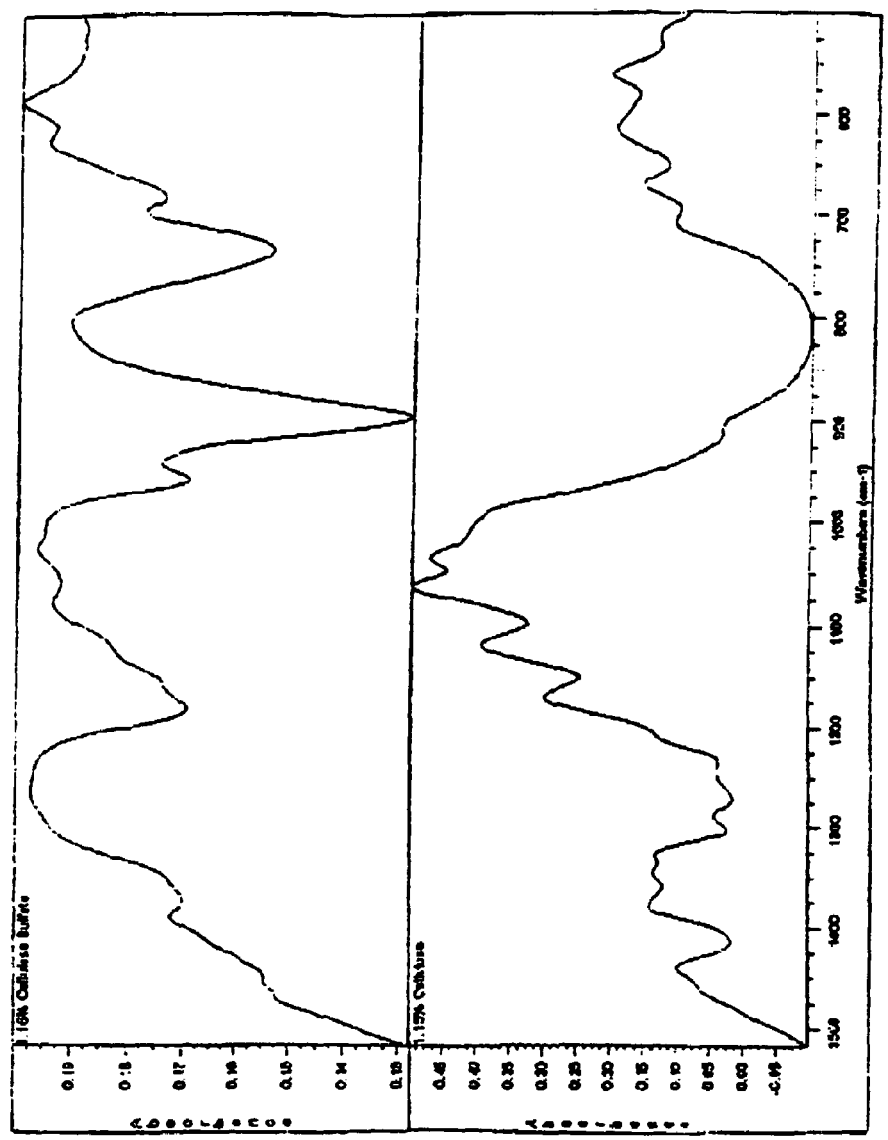
FIG. 3 is a FITR spectrum of a very high molecular weight sulfated polysaccharide of this invention.

The sample spectrum, (FIG. 3), can be visually inspected to verify the presence of certain characteristic absorptions. At about 800 $cm^{-1}$ there is a distinct peak due to C—O—S stretching and at about 1240 $cm^{-1}$ there is a distinct peak due to the S=O bond stretch. A reference spectrum of cotton linter, (FIG. 3, bottom), shows the presence of these new bonds due to the sulfate group.

EXAMPLE 7

This example demonstrates that very high molecular weight cellulose sulfate prepared by the method of this invention is an inhibitor of cholesterol uptake into cultured human Caco-2 cells.

Figure 4:
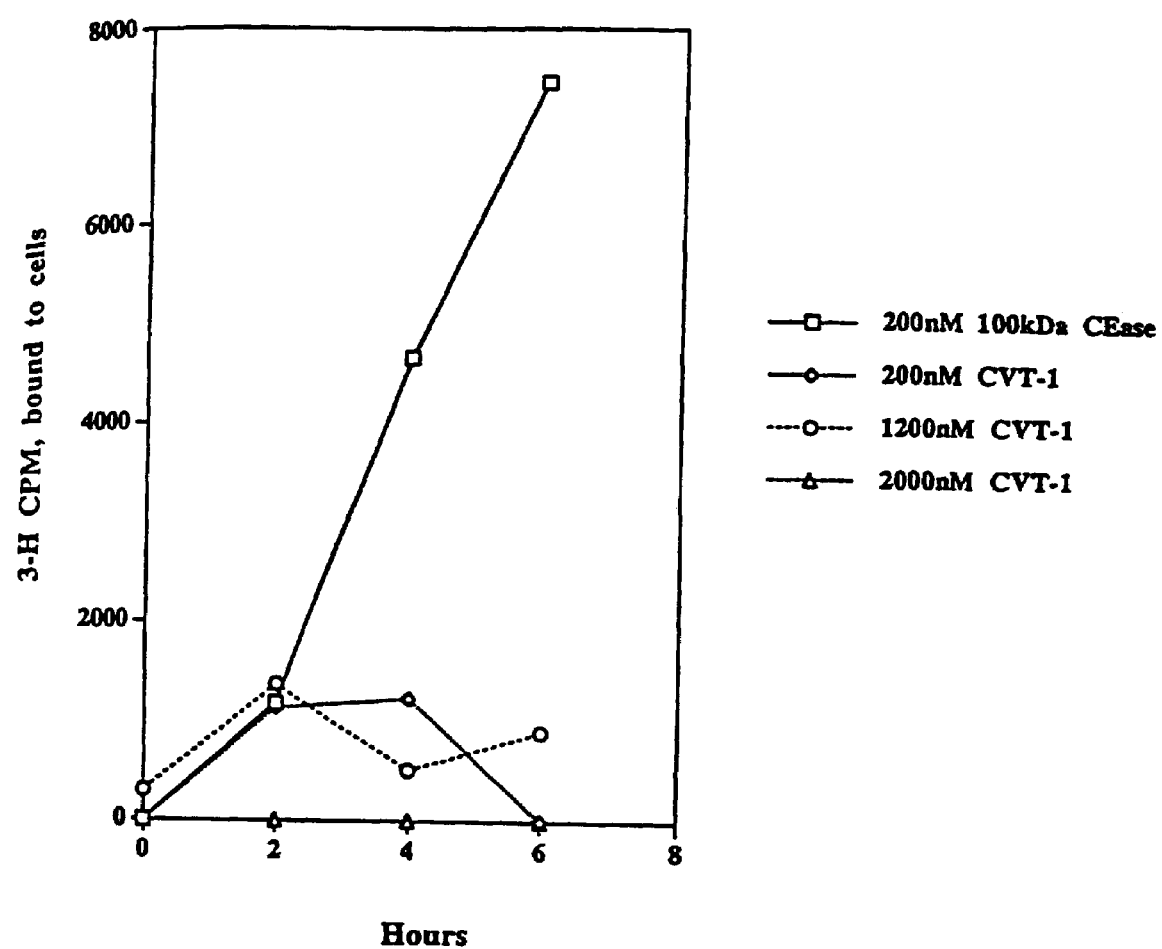
FIG. 4 is a plot of cholesterol uptake in Caco-2 cells over time.

Colonic adenocarcinoma cells (Caco-2 cells; American Type Culture Collection) were grown to confluence ($2.0 \times 10^6$ cells per well) in plastic wells (22.6 mm; 4 $cm^2$) and incubated overnight in Eagle's minimum essential medium and 10% lipoprotein deficient serum. The cells were rinsed once with 500 ml of PBS and then incubated with 8 mM sodium taurocholate, 1% bovine serum albumin and 1.0 pmole of [$^3$H] cholesterol incorporated in phosphatidylcholine vesicles and various concentrations of high molecular weight cellulose sulfate. The experiment was initiated with the addition of human cholesterol esterase to give a final enzyme concentration of 200 nM in a reaction volume of 500 µl. At various times, the reaction was quenched by removing the incubation medium and rinsing the cells with PBS. The cells were detached from the wells with 1% sodium dodecyl sulfate solution (200 µl) and the cellular debris counted to determine the amount of cholesterol associated with the cells. As shown in FIG. 4, incubation of homogeneous human pancreatic cholesterol esterase (200 nM) with [$^3$H]-cholesterol in liposomes in the presence of $2 \times 10^6$ Caco-2 cells led to incorporation of free cholesterol, an effect entirely eliminated in the presence of 200 nM cellulose sulfate.

EXAMPLE 8

In order for the very high molecular weight sulfated polysaccharides of this invention to interact with cholesterol esterase, they must first pass through the stomach where they can experience pH values less than 2.0. Since cellulose based compounds are less stable at acid pH, this investigation was carried out to demonstrate that degradation and loss in potency did not occur to a significant degree under simulated gastric conditions.

A 1.0 mg/ml solution of a very high molecular weight sulfated polysaccharide was prepared in a simulated gastric fluid (7 ml concentrated HCl, 3800 units pepsin and 2 g NaCl in 1 L of water), and a 1.5 µl aliquot was removed for analysis. The aliquot was immediately analyzed for its ability to inhibit the cholesterol esterase catalyzed hydrolysis of cholesterol [$^{14}$C]-oleate (Example 3) and its molecular weight was determined (Example 5). The remaining solution was placed in a 37° C. water bath, and time 0 was recorded as the test tube was placed in the bath. At 1 hr, 2 hr, and 25 hr, aliquots were removed and analyzed for potency, molecular weight and the percent with a molecular weight less than 75,000 Daltons. As shown in Table III, there is no change in $IC_{50}$ over a two hour incubation period and, moreover, there is little change in molecular weight. While the starting molecular weight was 5,000,000 Daltons, there is large error at these high values so there is probably no significant difference between this value and the values seen at 1 hr and 2 hr, 3,900,000 Daltons and 3,600,000 Daltons, respectively. However, after 25 hr, there is evidence of degradation with the molecular weight decreasing to 850, 000 Daltons, which is accompanied by a 3-fold increase in the $IC_{50}$ from 21 ng/ml to 68 ng/ml.

Another measure of degradation is the percentage of carbohydrate which appears below an arbitrary molecular weight. In this case, 75,000 Daltons was chosen since this is understood as the value above which no absorption occurs. As shown in Table III, after 2 hr, only about 1% of the sample is degraded to a molecular weight below this value, and even after 25 hr, this value has increased to only 3.4%.

TABLE III

STABILITY WITH PEPSIN AT pH 1.5 AND 37° C.

| TIME (hrs) | $IC_{50}$ (ng/ml) | Molecular Wt. (kDa) | % .75 kDa |
|---|---|---|---|
| 0 | 26 | 5000 | 0.0 |
| 1 | 23 | 3900 | 0.4 |
| 2 | 21 | 3600 | 1.1 |
| 25 | 68 | 850 | 3.4 |

Taken together, this example indicates that over the residence times commonly occurring in the stomach, the very high molecular weight sulfated polysaccharides of this invention do not lose their potency, and moreover, the sulfated polysaccharides are minimally degraded.

EXAMPLE 9

The objective of this study was to determine the amount of absorption of orally administered [$^{14}$C]-labeled, very high molecular weight sulfated polysaccharides in male rats. The [$^{14}$C]-labeled cellulose used in this study was isolated from cotton bolls which had been exposed to $^{14}CO_2$, and the polysaccharide was sulfated following the procedure given in Example 1.

Six male Sprague-Dawley rats were given a single 375 mg/kg dose of sulfated [$^{14}$C]-labeled cellulose by oral gavage (Table IV).

TABLE IV

DOSE SOLUTION ANALYSIS

| Parent Compound (mg/ml) | 25.0 |
|---|---|
| Radioactivity (DPM/ml) | 412898 |
| Radioactivity (µCi/ml) | 0.186 |
| Activity (DPM/mg) | 16516 |
| Total Dose Administered (mg) | 110 |

Following dose administration, animals were placed in Elizabethan collars and fitted with fecal cups to prevent fecal contamination of collected urine. Cumulative urine samples were collected from 0–4, 4–8, and 8–24 hours post-dose. Feces were removed from the fecal cups at 12 hours and 24 hours post-dose. Serial blood samples were obtained at 0.33, 1, 3, 6, 10, and 24 hours following dose administration. In addition, a thorough cage-wash was performed following the last sample collection. Derived plasma, urine, cage wash, feces and dose solution were assayed for radioactive content by oxidation followed by scintillation counting. The results were used to assess the oral absorption of radioactivity following single oral dose administration of high molecular weight sulfated [$^{14}$C]-cellulose.

Radioactivity levels were not detectable in any of the plasma, urine and cage wash samples collected during the study. From the amount of radioactivity administered and the detection limit of the method, in this study, greater than 99.5% of the very high molecular weight sulfated polysaccharide was not absorbed.

EXAMPLE 10

This example demonstrates the importance of controlling the sulfation reaction temperature between 13° and 20° C.

Cotton linter cellulose was received from Buckeye Cellulose (Memphis, Tenn.) and DMF-$SO_3$ complex was from Du Pont (large scale reactor) or Aldrich Chemical (bench scale).

The molecular weight of the cellulose sulfate polymer and the percentage with a molecular weight less than 75,000 Daltons were determined by HPLC gel permeation chromatography as described in Example 5. The degree of sulfation was determined using the conductometric titration described in Example 5.

Three samples (300 mg each) of minced cotton linters were soaked at 20° C. for 3 hour in 7.6 ml of anhydrous DMF. The flasks were immersed in water baths at 15° C., 20° C. and 25° C. After standing for 30 min to reach temperature equilibrium, 1.14 g of DMF-$SO_3$ complex dissolved in 2.5 ml DMF was added to each flask. After 3 hrs, the reactions were quenched by the addition of 915 mg of sodium bicarbonate followed by 25 ml of water. The samples were stirred at ambient temperature for 20 hours and then transferred to dialysis membranes (Molecular weight cut off 10,000 Daltons). The samples were dialyzed exhaustively against water, lyophilized and the following properties were determined: molecular weight, % with molecular weight less than 75,000 Daltons, degree of sulfation, and elemental analysis. As summarized in Table V below, a lower reaction temperature favors the formation of high molecular weight polymer with less low molecular weight contamination.

TABLE V

Properties of Cellulose Sulfate Synthesized at Different Temperatures

| Temp. | Mol. Wt (kDa) | % <75,000 Da | $SO_4$/Mon. | % Sulfur |
|---|---|---|---|---|
| 15 | 966 | 0.48 | 1.84 | 18.08 |
| 20 | 607 | 0.74 | 1.52 | 18.17 |
| 25 | 450 | 0.98 | 1.65 | 18.30 |

Sulfation of cotton linter cellulose was performed on a large scale under a blanket of nitrogen at a variety of temperatures following the procedure described in Example 1. The maximum reaction temperature was recorded and the results are summarized in Table VI below.

TABLE VI

Properties of Cellulose Sulfate Manufactured at Various Temperatures

| Test No. | Temp. Max | Mol. Wt. (kDa) | % <75 kDa | $SO_4$ to Monomer | Yield (%) |
|---|---|---|---|---|---|
| 1 | 16° | 6160 | <1 | 1.65 | 91 |
| 2 | 16° | 1526 | 16.1 | 2.01 | 85 |
| 3 | 17° | 3712 | 2.2 | 2.28 | 100 |
| 4 | 19° | 3300 | 0.0 | 1.65 | 62 |
| 5 | 20° | 1024 | 2.5 | 2.06 | 100 |
| 6 | 22° | 929 | 4.0 | 1.94 | 74 |
| 7 | 25° | 527 | 7.0 | 2.14 | 80 |
| 8 | 27° | 394 | 8.54 | 2.04 | 100 |
| 9 | 27° | 242 | 16.4 | 2.29 | 100 |
| 10 | 27° | 324 | 11.1 | 1.95 | 92 |

The results indicate that the yield and degree of sulfation are both insensitive to temperature over the narrow range of 16° C. to 27° C. The average degree of sulfation was 2.00, and under these reaction conditions, there was no trend indicating that temperature affects this parameter. On the other hand, as evidenced by the decrease in molecular weight, cellulose sulfate underwent marked depolymerization over this same narrow temperature range. Since low molecular weight polysaccharides can be absorbed by the small intestine, the presence of these reaction by-products are of more serious concern than the average molecular weight, and, as shown in the table above, the higher reaction temperature also favored the generation of these potentially toxic substances. Thus, when the maximum reaction temperature was 16° C.–19° C., only 1% to 2% of the sulfated material had a molecular weight less than 75,000 Daltons, while at 27° C. this value increased to 10%–15%. Taken together, these data indicate that when sulfation is carried out with DMF-SO$_3$ complex, the temperature of the sulfation reaction should be less than 20° C.

To define the minimum reaction temperature, the procedure described in Example 1 was followed except the reaction mixture was cooled to 1° C. (Step A) and the temperature was never allowed to exceed 13° C. throughout the 150 min reaction time. In every other way, the manufacturing run was identical to those described above. Following this procedure, the sulfated polysaccharide had a molecular weight of 5,000,000 Daltons, but the yield was only 18.5%. Therefore, to produce sulfated polysaccharide of high molecular weight and in good yield, the reaction temperature must be between 13° and 20° C.

EXAMPLE 11

Toxicity studies by the oral route have been carried out in rats and dogs with very high molecular weight sulfated polysaccharides of this invention. All studies reported here were conducted in compliance with the Good Laboratory Practice Regulation set forth in 21 CFR 58. Two types of studies were performed. First, an acute study (dosed every 2 hours for 24 hours) with a 14-day observation period was carried out in rats. Second, a chronic study was carried out in which high molecular weight sulfated polysaccharide was administered TID at daily dose levels of up to 1,125 mg/kg in the rat and of up to 2,700 mg/kg in the dog.

Acute Administration (Rat). Ten male and ten female CD® rats were assigned to either a control group or to a very high molecular weight sulfated polysaccharide treated group. Sulfated polysaccharide treated animals received by gavage 250 mg/kg every 2 hours throughout the course of the day for a total dose of 3,250 mg/kg. Control animals received an equivalent volume of vehicle (deionized water) only. In this acute study, the high viscosity of the drug limited the dose solution concentration to 25 mg/ml. Given the dose volumes administered (10 ml/kg) and the total number of doses received by each animal during the course of the day (13), the highest possible dose that could be administered in one day was 3,250 mg/kg. The animals were observed for 14 days and then subjected to necropsy. With the exception of transient soft stools in three animals, there were no adverse findings attributable to the drug. Parameters evaluated were mortality, morbidity, body weight, clinical signs and gross pathology. These results are found in Table VII below.

TABLE VII

Summary of Acute Oral Toxicity Study

| Group ID # | # of Animals | Treatment | Dosage | mg/kg/dose Cellulose Sulfate | mg/kg/total | Results |
|---|---|---|---|---|---|---|
| 1 | 10M, 10F | DI water | 10 ml/kg | 0 | 0 | No Adverse Effects |
| 2 | 10M, 10F | Cellulose Sulfate | 10 ml/kg | 250* | 3250 | No Adverse Effects** |

*Sulfated polysaccharides were administered every 2 hours over the course of 1 day.
**Three treated animals exhibited transient soft stools.

Chronic Administration (Rat). A very high molecular weight sulfated polysaccharide of this invention prepared by the method of Example 1 was administered orally by gavage to 2 groups of 15 male and 15 female Charles River CD® rats at dosage levels of 150 and 375 mg/kg three times daily for total dosage levels of 450 and 1,125 mg/kg/day. The control group, consisting of 15 male and 15 female animals, received vehicle (deionized water) on a comparable regimen. Following 28 days of treatment, 10 animals/sex/group were euthanized and five animals/sex/group were allowed to recover for 14 days, and then they were euthanized. Parameters evaluated were: mortality, clinical signs, body weight, food consumption, ophthalmoscopic examination, hematology, biochemistry, urinalysis, organ weights, and macroscopic and microscopic examination of designated tissues. Statistical analysis was conducted on body weight, food consumption, hematology, biochemistry, urinalysis parameters and organ weights. Criteria evaluated during the 14-day recovery period included all of the above except for ophthalmoscopic signs.

Following four weeks of treatment and two weeks of recovery, body weight, food consumption and food efficiency values from all treatment groups were comparable to those of the control groups with no significant trends. The results are found in Table VIII below.

TABLE VIII

Summary of 28-Day Oral Toxicity Study in CD Rats

| # of Animals | Dosage level (mg/kg/day)* | Dose Volume | Dose Solution | Duration (days) | Results |
|---|---|---|---|---|---|
| 15M, 15F | 0 | 15 ml/kg | DI water | 28 | NSE** |
| 15M, 15F | 450 | 15 ml/kg | 10 mg/ml | 28 | NSE |
| 15M, 15F | 1125 | 15 ml/kg | 25 mg/ml | 28 | NSE |

*Each dose was administered in 3 equal portions each day.
**NSE = No Significant Effects In summary, clinical pathology evaluation of all groups showed no test article-related findings in any of the treated groups. Anatomic pathology evaluation showed no test article-related organ weight changes and no test article-related microscopic observations in any organs or tissues examined.

Chronic Administration (Dogs). Very high molecular weight sulfated polysaccharides prepared following the method of Example 1 were administered orally for 28 days via gelatin capsules to groups of 3 to 4 purebred beagle dogs/sex at dosage levels of 100, 300 and 900 mg/kg TID for total dosage levels of 300, 900 and 2,700 mg/kg/day. The control group received empty gelatin capsules. Following 28 days of treatment, 3 dogs/sex/group were necropsied. The remaining 1 dog/sex in the control, 900 and 2,700 mg/kg/day groups were held for a 17-day recovery period and then euthanized.

Detailed clinical examinations were made once a week. All animals were observed for mortality, morbidity, and overt signs of toxicity twice a day and for pharmacotoxic signs just prior to dosing and about 2 hours post dose. Body weights and food consumption were recorded pretest and weekly. Complete physical examinations were conducted during pretest and at the end of the dosing and recovery phase. Ophthalmoscopic and electrocardiographic examinations were conducted during the acclimatization period and at the end of the dosing phase. Clinical pathology laboratory studies (hematology, serum biochemistry and urinalysis) were conducted once during pretest and at the end of the dosing and recovery periods. Complete macroscopic pathologic examinations were performed on all animals at the scheduled necropsies following the dosing and recovery periods. Absolute and relative organ weights were recorded for selected organs. Microscopic examinations were performed on selected tissues for all control and high dose animals.

All of the animals survived to study termination. Test article-related clinical signs included transient emesis in one male and soft stool and unformed feces of liquid consistency. The incidence of emesis was increased in males at the 2,700 mg/kg/day dosage level in comparison to the controls. A dosage-related increase in soft stool was noted, mainly at the 900 and 2,700 mg/kg/day dosage levels. Male and female dogs receiving 2,700 mg/kg/day had markedly increased incidence of unformed liquid stools relative to controls; the incidences observed in the 300 and 900 mg/kg/day dosage level groups were marginally increased compared to controls. In spite of these findings, no meaningful differences were observed in body weights or food consumption during the 4-week dosing period. During the recovery period, the incidence of these clinical signs were similar in all groups. The results of the testing are shown in Table IX below.

TABLE IX

| # of Animals | Dosage Level (mg/kg/day)* | Dose Volume | Capsule Volume | Duration (days) | Results |
|---|---|---|---|---|---|
| 4M, 4F | 0 | 4 capsules | empty | 28 | NAE** |
| 3M, 3F | 300 | 4 capsules | BPC*** | 28 | NAE |
| 4M, 4F | 900 | 4 capsules | BPC | 28 | loose stools |
| 4M, 4F | 2700 | 4 capsules | BPC | 28 | loose stools**** |

*Each dose was administered in 3 equal portions each day.
**NAE = No Adverse Effects.
***High molecular weight sulfated polysaccharide.
****Transient emesis was noted in one male.

No toxicologically significant or test article-related findings were noted in the following: physical, ophthalmoscopic and electrocardiographic examinations; hematological, biochemical and urological parameters; organ weights; macroscopic and microscopic pathology. Thus, no evidence of systemic toxicity was detected in male and female dogs after 28 days of oral dosing of high molecular weight sulfated polysaccharides via capsule at levels up to 900 mg/kg TID (2,700 mg/kg/day).

EXAMPLE 12

A very high molecular weight sulfated polysaccharide of this invention, prepared by the method of Example 1, was tested for mutagenic activity in the *Salmonella-Escherichia coli*/mammalian-microsome reverse mutation assay, in the L5178Y TK+/−mouse lymphoma forward mutation assay and in an in vivo mouse micronuclease assay.

*Salmonella-Escherichia coli*/Mammalian-Microsome Reverse Mutation Assay (Ames Test). This assay evaluates the high molecular weight sulfated polysaccharide and/or its metabolites for their ability to induce reverse mutations in the genome of specific *Salmonella typhimurium* tester strains and an *Escherichia coli* tester strain, both in the presence and absence of an exogenenous metabolic activation system of mammalian microsomal enzymes derived from Aroclor™ induced rat liver (S9). The tester strains used in the mutagenicity study were *Salmonella typhimurium* TA98, TA100, TA1535, TA1537, TA1538 and *Escherichia coli* tester strain WP2uvrA$^-$. Each assay was conducted using six doses of high molecular weight sulfated polysaccharide, three plates per dose, along with a concurrent vehicle (deionized water) and positive and negative controls in both the presence and absence of S9 mix. The doses of test artice tested in this study were 66.7, 100, 333, 667, 1,000 and 1,500 µg per plate. The experimental findings are shown in Table X below.

TABLE X

Summary of Results of the Ames Test

| Organisms | HSP* (µg/plate) | S9 | Results |
|---|---|---|---|
| *S. typh.* | | | |
| TA 98 | 67–1,500 | + | − |
| TA 98 | 67–1,500 | − | − |
| TA 100 | 67–1,500 | + | − |
| TA 100 | 67–1,500 | − | − |
| TA 1535 | 67–1,500 | + | − |
| TA 1535 | 67–1,500 | − | − |
| TA 1537 | 67–1,500 | + | − |
| TA 1537 | 67–1,500 | − | − |
| TA 1538 | 67–1,500 | + | − |
| TA 1538 | 67–1,500 | − | − |
| *E. coli* | | | |
| WP2uviA | 67–1,500 | + | − |
| WP2uviA | 67–1,500 | − | − |

*HSP High molecular weight sulfated polysaccharide

The results in Table X indicate that under the conditions of this study high molecular weight sulfated polysaccharides do not cause a positive increase in the number of revertants per plate of any of the tester strains either in the presence or absence of microsomal enzymes prepared from rat liver (S9).

Mouse Lymphoma Forward Mutation Assay. This in vitro assay evaluates the ability of test articles to induce forward mutations at the thymidine kinase (TK) locus in the mouse lymphoma L5178Y cell line. A single mutation assay was performed for both nonactivation and rat liver S9 metabolic activation conditions. Six treatments from 500 µg/ml to 5000 µg/ml were initiated with and without activation. At most, weak cytotoxicities were induced. Under nonactivation and activation conditions, none of the six assayed treatments induced a mutant frequency that exceeded the minimum criterion for a positive response and no dose-related trend was observed. Therefore, high molecular weight sulfated polysaccharides are considered to be negative for inducing forward mutations at the TK locus in L5178Y mouse lymphoma cells under the nonactivation and S9 metabolic activation conditions used in this study.

In Vivo Mouse Micronuclease Assay. This assay evaluates the ability of test articles to induce micronuclei in bone marrow polychromatic erythrocytes of CD-1 (ICR) mice. For the assay, high molecular weight sulfated polysaccharide dose levels of 800, 1600 and 3200 mg/kg were selected. Ten animals (five males and five females) were randomly assigned to each dose/harvest time group and dosed at 40 ml/kg. Positive control groups were euthanized approximately 24 hours after dosing. The animals dosed with the high molecular weight sulfated polysaccharide were euthanized at 24, 48 and 72 hours after dosing for extraction of the bone marrow. The experimental findings are shown in Table XI below.

humans in an amount of about 1000 mg at or about meal time lowers both total cholesterol and LDL.

Five human subjects comprising males or females between the ages of 21–70 were selected for the study population. Excluded from the population were persons having a history of medical disease and drug abuse, females with child bearing potential, any subject who had taken a dose of any medication within two weeks of the study, any person with a body weight more than 30% above or 20% below Metropolitan Life Insurance Co. Tables, any subject who uses or used tobacco products in the past year, and any person who is a subject in another therapeutic agent trial or who has been in the last 30 days.

An essentially non-absorbable very high molecular weight sulfated polysaccharide as prepared in Example 1 was supplied in powdered form and 1000 mg were added to 8 ounces of a prepared commercial diet soft drink (such as CRYSTAL LIGHT®) that was previously mixed in boiling water. The powdered sulfated polysaccharide was stirred into the liquid mixture for up to twenty minutes or until it

TABLE XII

Micronucleas Test Data Summary

| Treatment | Dose | Harvest Time (HR) | % Micronucleated PCEs** Mean of 1000 per animal ± S.E. | | |
|---|---|---|---|---|---|
| | | | Males | Females | Total |
| Vehicle Control Sterile Deionized Water | 40 mg/kg | 24 | 0.00 ± 0.00 | 0.02 ± 0.02 | 0.01 ± 0.01 |
| | | 48 | 0.04 ± 0.04 | 0.06 ± 0.04 | 0.05 ± 0.03 |
| | | 72 | 0.04 ± 0.02 | 0.04 ± 0.02 | 0.04 ± 0.02 |
| Positive Control Cyclophosphamide | 80 mg/kg | 24 | 2.20 ± 0.46* | 2.22 ± 0.25* | 2.21 ± 0.25* |
| HSP*** | 800 mg/kg | 24 | 0.00 ± 0.00 | 0.08 ± 0.06 | 0.04 ± 0.03 |
| | | 48 | 0.08 ± 0.06 | 0.06 ± 0.04 | 0.07 ± 0.03 |
| | | 72 | 0.02 ± 0.02 | 0.12 ± 0.06 | 0.07 ± 0.03 |
| | 1600 mg/kg | 24 | 0.10 ± 0.06 | 0.08 ± 0.04 | 0.09 ± 0.03 |
| | | 48 | 0.02 ± 0.02 | 0.00 ± 0.00 | 0.01 ± 0.01 |
| | | 72 | 0.02 ± 0.02 | 0.02 ± 0.02 | 0.02 ± 0.01 |
| | 3100 mg/kg | 24 | 0.02 ± 0.02 | 0.00 ± 0.00 | 0.01 ± 0.01 |
| | | 48 | 0.06 ± 0.04 | 0.02 ± 0.02 | 0.04 ± 0.02 |
| | | 72 | 0.04 ± 0.04 | 0.00 ± 0.00 | 0.02 ± 0.02 |

**PCE Polychromatic Erythrocyte.
***HSP High Molecular Weight Sulfated Polysaccharide.

From these data, it is concluded that the high molecular weight sulfated polysaccharide used here does not induce a significant increase in micronuclei in bone marrow polychromatic erythrocytes under the conditions of this assay, and it is considered negative in the mouse bone marrow micronucleus test.

EXAMPLE 13

We have found that administering a very high molecular weight sulfated polysaccharide as prepared in Example 1 to went into solution. Finally, the solution was allowed to cool before administration to the human subject.

The prepared dose was administered three times per day just prior to a meal at 8:00 AM, 12 noon, and 6:00 PM. This exact dosing schedule was followed for each of the 7 days of the trial.

Serum samples were taken from each subject immediately before the first dose, at day 1, day 4, day 8, and day 14 and each sample was analyzed for total cholesterol and LDL. The results are found in Table XII below.

TABLE XII

| | 1000 mg Dosage Results* | | | | | | | |
|---|---|---|---|---|---|---|---|---|
| | Baseline | | Day 4 | | Day 8 | | Day 14 | |
| Subject No. | Total Chol. | LDL | Total Chol. | LDL | Total Chol. | LDL | Total Chol. | LDL |
| 1 | 185 | 128 | 170 | 122 | 183 | 128 | 169 | 115 |
| 2 | 252 | 194 | 229 | 176 | 226 | 148 | 230 | 156 |
| 3 | 253 | 173 | 254 | 205 | 247 | 186 | 234 | 151 |

TABLE XII-continued 1000 mg Dosage Results*

| | Baseline | | Day 4 | | Day 8 | | Day 14 | |
|---|---|---|---|---|---|---|---|---|
| Subject No. | Total Chol. | LDL | Total Chol. | LDL | Total Chol. | LDL | Total Chol. | LDL |
| 4 | 209 | 152 | 192 | 141 | 197 | 140 | 186 | 129 |
| 5 | 188 | 132 | 164 | 121 | 168 | 117 | 149 | 95 |
| Σ | 1087 | 779 | 1009 | 765 | 1021 | 719 | 968 | 646 |
| mean | 217 | 156 | 202 | 153 | 204 | 144 | 194 | 129 |
| std. dev. | 33 | 28 | 39 | 37 | 32 | 26 | 37 | 25 |

*mg/dl.

The same analyses were performed on a group of subjects taking a placebo (only CRYSTAL LIGHT®) in the same manner as that described above. These placebo results are found in Table XIII below.

TABLE XIII

Placebo Dosage Results*

| | Baseline | | Day 4 | | Day 8 | | Day 14 | |
|---|---|---|---|---|---|---|---|---|
| Subject No. | Total Chol. | LDL | Total Chol. | LDL | Total Chol. | LDL | Total Chol. | LDL |
| 302 | 223 | 153 | 219 | 134 | 197 | 143 | 205 | 141 |
| 305 | 154 | 97 | 155 | 99 | 152 | 106 | 166 | 108 |
| 307 | 149 | 100 | 142 | 90 | 133 | 86 | 166 | 108 |
| 310 | 296 | 219 | 275 | 183 | 259 | 183 | 275 | 201 |
| 313 | 244 | 175 | 245 | 166 | 230 | 158 | 222 | 141 |
| 316 | 272 | 190 | 257 | 167 | 265 | 175 | 261 | 190 |
| 317 | 251 | 157 | 259 | 176 | 296 | 203 | 276 | 194 |
| 321 | 228 | 154 | 228 | 155 | 241 | 153 | 202 | 125 |
| 233 | 199 | 146 | 190 | 133 | 194 | 122 | 202 | 139 |
| 326 | 177 | 114 | 174 | 100 | 155 | 82 | 162 | 100 |
| 329 | 251 | 167 | 235 | 145 | 220 | 141 | 236 | 163 |
| 331 | 240 | 175 | 224 | 163 | 213 | 135 | 235 | 145 |
| Σ | 2684 | 1647 | 2603 | 1711 | 2555 | 1678 | 2608 | 1755 |
| mean | 224 | 154 | 217 | 143 | 213 | 140 | 217 | 146 |
| std. dev. | 46 | 36 | 43 | 32 | 49 | 37 | 41 | 35 |

*mg/dl.

The cholesterol levels from the placebo experiment and from the high molecular weight sulfated polysaccharide are summarized in Table XIV below.

TABLE XIV

Comparison of Placebo and HSP* on Serum and LDL-Cholesterol Levels**

| | Total Cholesterol | | LDL-Cholesterol | |
|---|---|---|---|---|
| Time | Placebo | HSP* | Placebo | HSP* |
| Baseline | 224 | 217 | 154 | 156 |
| Day 4 | 217 | 202 | 143 | 153 |
| Day 8 | 213 | 204 | 140 | 144 |
| Day 14 | 217 | 194 | 146 | 129 |

*HSP High molecular weight sulfated polysaccharide
**mg/dl

The data indicate that the high molecular weight sulfated polysaccharide manufactured according to Example 1 lowers serum cholesterol 10.6% from 217 mg/dl to 194 mg/dl and it also lowers LDL-cholesterol 17.3% from 156 mg/dl to 129 mg/dl.

What is claimed is:

1. A method for lowering serum cholesterol in humans comprising administering to a human the combination of an essentially non-absorbable very high molecular weight sulfated polysaccharide having less than about 0.98 wt. percent of sulfated polysaccharides having a molecular weight less than 75,000 Daltons and containing less than 0.5 weight percent of inorganic sulfate and a second compound that reduces serum cholesterol levels wherein the high molecular weight sulfated polysaccharide is prepared by sulfating a very high molecular weight polysaccharide with a sulfur containing compound at a temperate less than about 20° C.

2. The method of claim 1 wherein the second compound is at least one cholesterol synthesis blocker.

3. The method of claim 2 wherein the cholesterol synthesis blocker is lovastatin.

4. The method of claim 1 wherein the second compound is an inhibitor of ACAT.

5. The method of claim 1 wherein the sulfated polysaccharide is sulfated cellulose.

6. A method for lowering serum cholesterol in humans comprising administering to a human the combination of an essentially non-absorbable very high molecular weight sulfated cellulose having less than about 0.98 wt. percent of sulfated cellulose having a molecular weight less than 75,000 Daltons and containing less than 0.5 weight percent of inorganic sulfate and lovastatin wherein the high molecular weight sulfated polysaccharide is prepared by sulfating a very high molecular weight polysaccharide with a sulfur containing compound at a temperature less than about 20° C.

* * * * *